(12) United States Patent
Schoutens (10) Patent No.: US 9,089,346 B2
(45) Date of Patent: Jul. 28, 2015

(54) SURGICAL DRILL BITS

(71) Applicant: DePuy Synthes Products, Inc., Raynham, MA (US)

(72) Inventor: Robert J. Schoutens, Oberdorf (CH)

(73) Assignee: DePuy Synthes Products, Inc., Raynham, MA (US)

( * ) Notice: Subject to any disclaimer, the term of this patent is extended or adjusted under 35 U.S.C. 154(b) by 204 days.

(21) Appl. No.: 13/777,118

(22) Filed: Feb. 26, 2013

(65) Prior Publication Data

US 2013/0274750 A1    Oct. 17, 2013

Related U.S. Application Data

(60) Provisional application No. 61/623,218, filed on Apr. 12, 2012.

(51) Int. Cl.
*A61B 17/00* (2006.01)
*A61B 17/16* (2006.01)

(52) U.S. Cl.
CPC .................................. *A61B 17/1615* (2013.01)

(58) Field of Classification Search
CPC combination set(s) only.
See application file for complete search history.

(56) References Cited

U.S. PATENT DOCUMENTS

| | | |
|---|---|---|
| 3,665,801 A | 5/1972 | Gutshall |
| 3,806,270 A | 4/1974 | Tanner et al. |
| 4,080,093 A | 3/1978 | Maier |
| 5,486,075 A | 1/1996 | Nakamura et al. |
| 5,678,960 A | 10/1997 | Just et al. |
| 2009/0016832 A1* | 1/2009 | Onose et al. ............. 408/59 |
| 2012/0004661 A1 | 1/2012 | Leppelmeier |
| 2012/0039680 A1 | 2/2012 | Koike et al. |

OTHER PUBLICATIONS

International Patent Application No. PCT/US2013/027747: International Search Report dated Aug. 5, 2013, 15 pages.
Oh et al., "Effect of implant drill characteristics on heat generation in osteotomy sites: a pilot study," Clin. Oral Implants Res., Jul. 2011, 22(7), 722-726.

* cited by examiner

*Primary Examiner* — Sameh Boles
(74) *Attorney, Agent, or Firm* — Baker & Hostetler LLP (57) ABSTRACT

A surgical drill bit can include a body portion that defines a central axis that extends along a first direction. The body portion can be separated along the first direction into a distal cutting segment, and a guiding segment. The body portion can include a helical flute that winds about the central axis. The helical flute can define a first outer profile along the cutting segment and a second outer profile along the guiding segment, the first outer profile has a first leading edge and a first bearing surface and the second outer profile has a second leading edge and a second bearing surface. The first leading edge can be configured to cut into bone and can be spaced from the central axis by a first length. The second leading edge can be spaced from the central axis by a second length that is less than the first length.

34 Claims, 5 Drawing Sheets

SURGICAL DRILL BITS

CROSS REFERENCE TO RELATED APPLICATIONS

This application claims the benefit of U.S. Provisional Application No. 61/623,218 filed Apr. 12, 2012 the contents of which are hereby incorporated by reference in their entirety herein.

BACKGROUND

Certain medical procedures, such as osteosynthesis, are performed to stabilize and join bone segments to each other. Such procedures use stabilizing members such as rods or metal plates that are coupled to the bone segments by fixation elements such as bone screws, tacks, rivets, etc. Prior to the insertion of the bone screws into the bone segments, holes are pre-drilled into the bone segments using a surgical drill.

Various surgical drills are currently in use that facilitate the user to drill at many speeds from several rpms up to and possible exceeding 90,000 rpms. Because of the varying speeds, the drill can behave like a milling tool and cuts into the wall of the hole thereby unintentionally and undesirably widening the diameter of the hole. This cutting effect can be compounded by chatter, vibration, axial torsion by the user, and bone quality, each of which can cause the drill to counter rotate (i.e. wobble) about a center axis of the hole. In some cases, the hole diameter increases up to 30% of the desired hole diameter. Moreover, because of the high speed in which such drills operate, heat can build up thereby causing thermal damage in the bone segments. Therefore, current drill bits not only have problems with creating repeatable hole sizes but also harm the surrounding bone while the holes are being formed. For at least these reasons, the bone screws used during osteosynthesis fixation are at risk to a degraded performance due to the unintentional loss of bone caused by standard drill bits.

SUMMARY

In an embodiment, a surgical drill bit can be configured to form a hole in an anatomical structure. The surgical drill bit can include an elongate cylindrical body portion that defines a proximal end, a distal end spaced from the proximal end along a first direction, and a central axis that extends along the first direction. The body portion can be separated along the first direction into a distal cutting segment, and a guiding segment that is proximal to the cutting segment. The body portion can include at least one helical flute that winds about the central axis from the distal end to the proximal end. The at least one helical flute can define a first outer profile along the cutting segment and a second outer profile along the guiding segment, the first outer profile can have a first leading edge and a first bearing surface and the second outer profile can have a second leading edge and a second bearing surface. The first leading edge can be configured to cut into bone and can merge with the first bearing surface such that both the first leading edge and the first bearing surface are spaced from the central axis by a first length so as to define a first radius that is substantially equal to a radius of the hole to be formed. The second leading edge can be spaced from the central axis by a second length that is less than the first length and the second bearing surface is spaced from the central axis so as to define a second radius that is substantially equal to the first radius. The second outer profile can further include a substantially straight joining surface that connects the second leading edge to the second bearing surface such that the joining surface is angled radially inward with respect to a tangent of the second bearing surface by a first angle.

BRIEF DESCRIPTION OF THE DRAWINGS

The foregoing summary, as well as the following detailed description of the preferred embodiments of the application, will be better understood when read in conjunction with the appended drawings. For the purposes of illustrating the present disclosure, there is shown in the drawings preferred embodiments. It should be understood, however, that the application is not limited to the specific embodiments and methods disclosed, and reference is made to the claims for that purpose. In the drawings:

DETAILED DESCRIPTION

Certain terminology is used in the following description for convenience only and is not limiting. The words "right", "left", "lower" and "upper" designate directions in the drawings to which reference is made. The words "proximally" and "distally" refer to directions toward and away from, respectively, the surgeon using the surgical instrument. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

Figure 1:
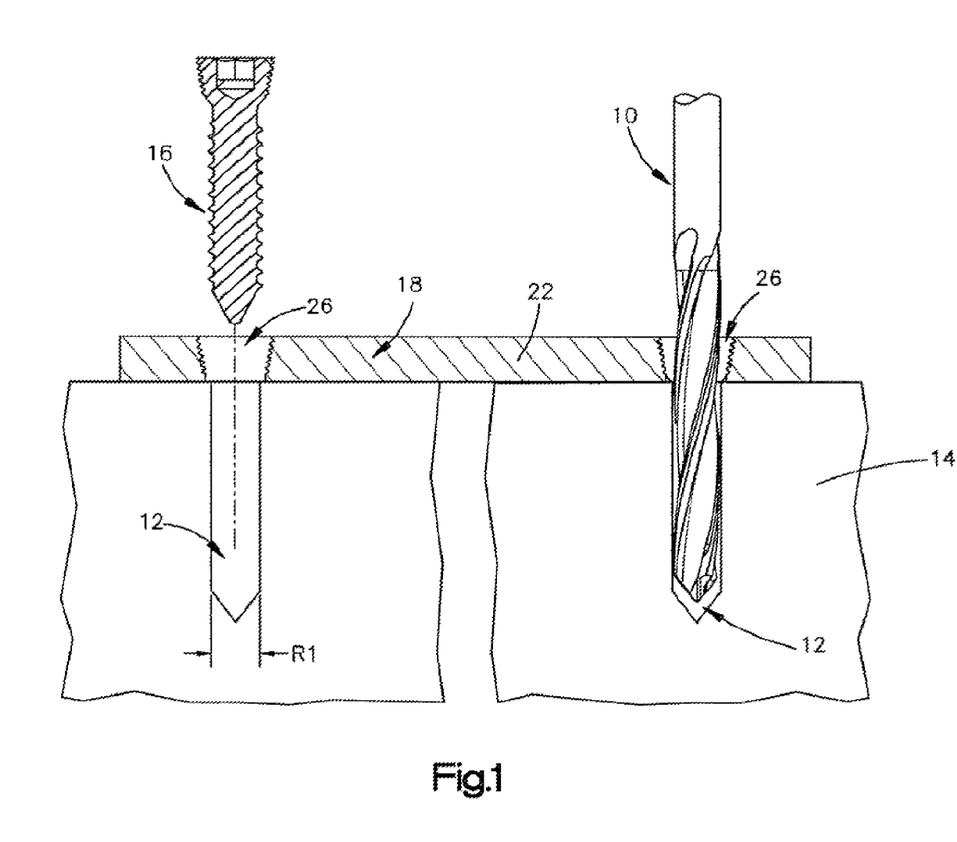
FIG. 1 is a side elevation view of a surgical drill bit according to an embodiment, the surgical drill bit being inserted through a hole of a bone plate so as to form a hole into a first bone segment.

As shown in FIG. 1, a surgical drill bit 10 is configured to be mounted to a drill and is further configured to form or otherwise cut a hole 12 into an anatomical structure 14 such as a bone fragment or a vertebral body. The hole 12 that is to be formed by the surgical drill bit 10 can be configured to receive a fixation element such as a screw 16 to thereby affix a load carrier 18 to the bone fragment 14. The hole 12 can be formed to have a hole radius $R_1$ that is sized to allow the screw 16 to securely affix the load carrier 18 to the anatomical structure 14. The load carrier 18 can be a bone plate 22 having a plurality of through holes 26, as illustrated, or the load carrier 18 can be any structure configured to affix two anatomical structures relative to each other. The surgical drill bit 10 can be configured to advance through one of the through holes 26 of the bone plate 22 as the hole 12 is being formed in the anatomical structure 14 or the surgical drill bit 10 can form the hole 12 prior to placement of the bone plate 22. It should be appreciated, however, that the surgical drill bit 10 can be configured to form or otherwise cut a hole into any anatomical structure. For example, the drill bit 10 can be configured to form a hole in an implant, such as in a spacer body of a vertebral implant. Moreover, it should be appreciated, that the holes 12 to be formed by the drill bit 10 can be configured to receive other fixation elements, such as Kirschner wires, rivets, or tacks, for example. It should also be appreciated that the through holes 26 can define a diameter that is substantially equal to a diameter of the surgical drill bit 10. It should also be appreciated that the hole 12 can be formed on its own without the drill bit 10 first advancing through a structure such as through the through hole 26 of the bone plate 22.

The surgical drill bit 10 can be configured to operate at a variety of speeds from several rpms up to and possibly exceeding 90,000 rpms. The surgical drill bit 10 is configured to maintain the size (i.e. the radius $R_1$) of the hole 12 at various speeds without substantial cutting into the wall of the hole 12 due to chatter, vibration, and/or axial torsion from the user. For example, the surgical drill bit 10 can maintain the size (i.e. the radius $R_1$) of the hole 12 to within about 6% of the desired size when the surgical drill bit 10 is operating at 60,000 rpms. The surgical drill bit 10 is also configured to reduce wall friction between the surgical drill bit 10 and the wall of the hole 12. The reduced friction may permit the use of high speeds while drilling which otherwise may cause thermal damage such as necrosis in the bone fragment due to the potential of heat buildup.

The surgical drill bit 10 can be made of metal such as steel for example. The surgical drill bit 10 can also be coated with a coating. For example, the surgical drill bit 10 can be coated with a titanium nitride coating, a diamond like carbon coating, or a nickel coating. It should be appreciated, however, that the surgical drill bit 10 can be made of any material as desired, and may be coated with any material as desired. Moreover, it should be appreciated that the drill bit 10 can be void of a coating as desired.

Figure 2A:
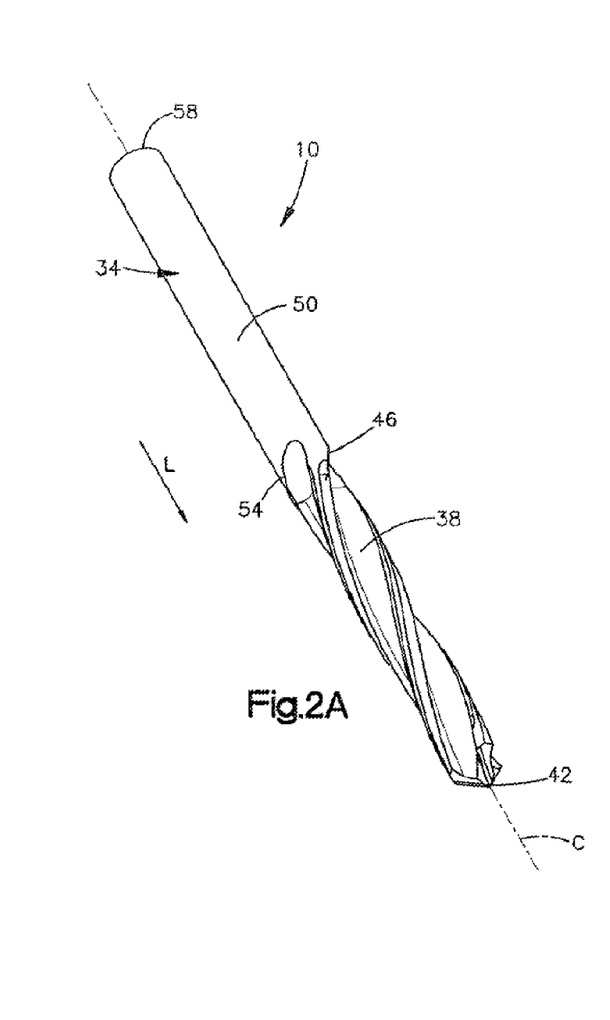
FIG. 2A is a perspective view of the surgical drill bit of FIG. 1, the surgical drill bit including a body portion that is elongate along a first direction and is separated along the first direction into a distal cutting segment and a proximal guiding segment, the body portion including three helical flutes wound about a central axis of the body portion and along the entire length of the body portion.
Figure 2B:
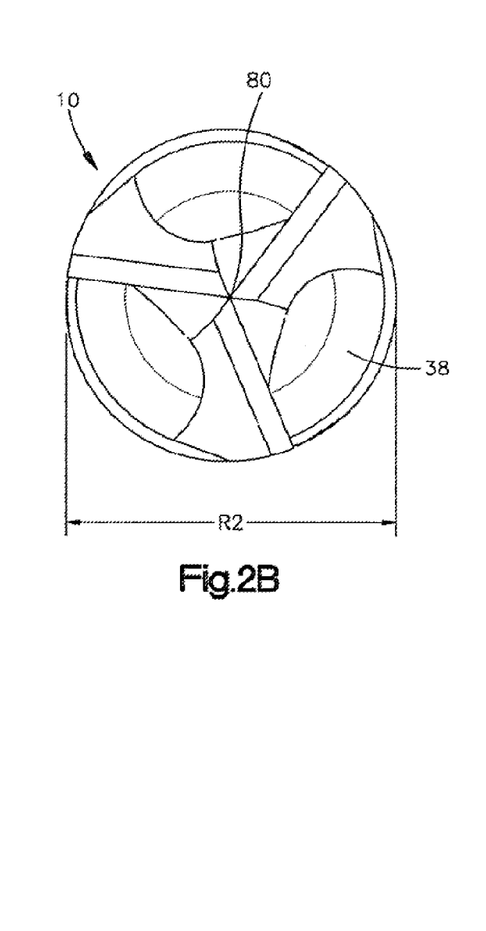
FIG. 2B is a bottom plan view of the surgical drill bit shown in FIG. 2A.
Figure 2C:
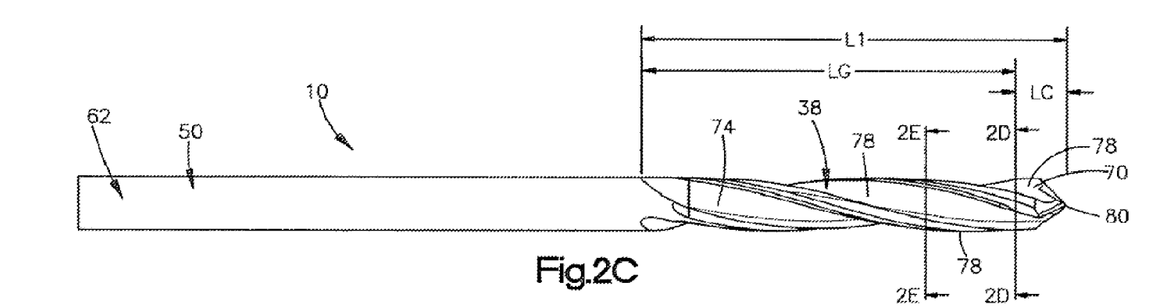
FIG. 2C is a side elevation view of the surgical drill bit shown in FIG. 2A.

As shown in FIGS. 2A-2C, the surgical drill bit 10 includes a body 34 that is elongate along a longitudinal direction L. The body 34 includes a first cylindrical body portion 38 that is elongate along the longitudinal direction L and defines a distal end 42, and a proximal end 46 spaced from the distal end 42 along the longitudinal direction L. The body 34 further includes a second body portion 50 that extends from the proximal end 46 of the first body portion 38. The second body portion 50 defines a distal end 54 and a proximal end 58 that is spaced from the distal end 54 along the longitudinal direction L. The first body portion 38 and the second body portion 50 further define a central axis C that extends along the longitudinal direction L. The first body portion 38 and the second body portion 50 can be integrally formed as a monolithic unit.

As shown in FIG. 2B, the surgical drill bit 10 and in particular the first body portion 38 has an outer radius $R_2$ that is substantially equal to the radius $R_1$ of the hole 12 to be formed. The surgical drill bit 10 can have any radius $R_2$ as desired. For example, the outer radius $R_2$ can be between about 1 mm and about 3 mm. It should be appreciated, however, that the drill bit 10 can be any size as desired and that the outer radius $R_2$ of the first body portion 38 can vary along the length of the first body portion 38. Moreover, the outer radius of the second body portion 50 can be different than the outer radius of the first body portion 38. For example, the outer radius of the second body portion 50 can be greater than or less than the outer radius of the first body portion 38.

As shown in FIG. 2C, the first body portion 38 is configured to form the hole 12 and the second body portion 50 is configured to provide a feature that allows the drill bit 10 to be coupled to a drill (powered or manual). As shown, the second body portion 50 can be cylindrical and can include a surface 62 that is configured to be gripped by a coupling feature of a drill. It should be appreciated, however, that the second body portion 50 can have other shapes and can include other features that are configured to be gripped by a drill. For example, the second body portion 50 can be at least partially hexagonal shaped. Therefore, it should also be appreciated, that the second body portion 50 can define a dimension that is not a radius.

Figure 2D:
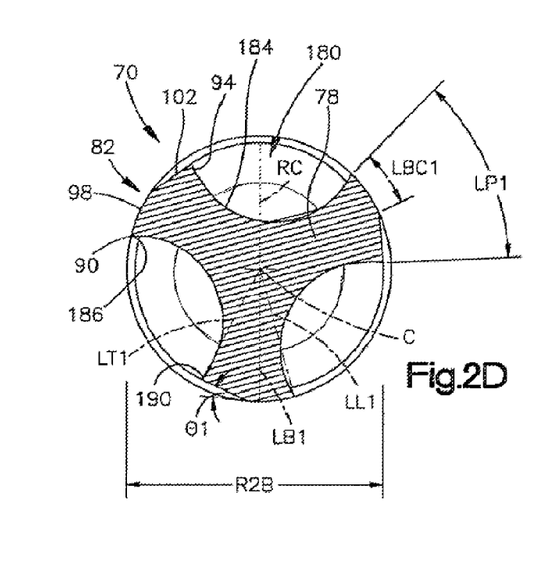
FIG. 2D is a cross-sectional view of the surgical drill bit shown in FIG. 2C through the line 2D-2D and showing an outer profile of the flutes along the cutting segment of the body portion.
Figure 2E:
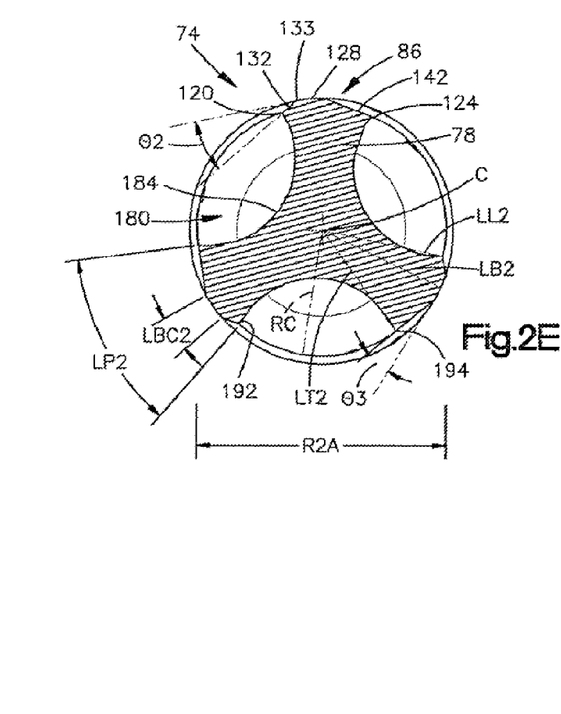
FIG. 2E is a cross-sectional view of the surgical drill bit shown in FIG. 2C through the line 2E-2E and showing an outer profile of the flutes along the guiding segment of the body portion.

As shown in FIGS. 2C-2E, the first body portion 38 is separated along the longitudinal direction L into a distal cutting segment 70, and a guiding segment 74 that is proximal to the cutting segment 70. The first body portion 38 can include at least one, such as three helical flutes 78 that wind about the central axis C from the distal end 42 to the proximal end 46 of the first body portion 38. As shown, the distal end 42 of the first body portion 38 defines a cutting tip 80. While the first body portion 38 is illustrated as including three helical flutes 78 it should be appreciated that the first body portion 38 can include any number of flutes 78 as desired. For example, the first body portion 38 can include two or four helical flutes 78 as desired. The flutes 78 can be substantially identical to each other as illustrated. It should be appreciated, however, that the flutes 78 can be different from each other as desired. For example, the distance by which the flutes 78 are spaced from the central axis can vary along the length of the guiding segment 74 such that each flute 78 is out of phase with at least one of the other flutes 78.

As shown in FIG. 2C, the first body portion 38 can have an overall length $L_1$ measured along the longitudinal direction L, and the guiding segment 74 can be a substantial portion of that overall length $L_1$. That is, the cutting segment 70 can define a cutting segment length $L_C$ and the guiding segment 74 can define a guiding segment length $L_G$, each measured along the longitudinal direction L. As shown, the guiding segment length $L_G$ is substantially greater than the cutting segment length $L_C$. For example, the cutting segment length $L_C$ can be less than 25% of the overall length $L_1$ of the first body portion 38. Moreover, it can be said that the cutting segment length $L_C$ is less than 35% of the guiding segment length $L_G$. It should be appreciated, however, that the cutting segment 70 and the guiding segment 74 of the first body portion 38 can have any lengths as desired. For example, the cutting segment length $L_C$ can be less than 10% of the overall length $L_1$ of the first body portion 38 as desired. Moreover it should be appreciated that the length of the cutting segment relative to the guiding segment can depend on the overall length and size of the surgical drill bit 10.

Both the cutting segment 70 and the guiding segment 74 can define the radius $R_2$. It should be appreciated, however, that the guiding segment 74 can have an outer radius $R_{2A}$ that is less than an outer radius $R_{2B}$ of the cutting segment 70. For example, the outer radius $R_{2A}$ of the guiding segment 74 can be between 100% to about 50% of the outer radius $R_{2B}$ of the cutting segment 70. Preferably, the outer radius $R_{2A}$ is about 0.1 mm less than the outer radius $R_{2B}$ Moreover, it should be appreciated, that a distal end of the guiding segment 74 can have a first radius while the proximal end can have a second radius that is less than the first radius such that the outer radius of the guiding segment 74 tapers from the distal end toward the proximal end. The taper can be a smooth taper, or the taper can be stepped, such that the drill bit defines a plurality of steps, each step having a different diameter. That is, the drill bit can have a plurality of steps such that each step increases in diameter from a distal most step of the plurality of steps to a proximal most step of the plurality of steps. It should be appreciated, that the smaller outer radius $R_{2B}$ can be formed by any desired machining methods such as milling, bead blasting, chemical etching, grounding, etc.

Now in reference to FIGS. 2C-2E, each helical flute 78 defines a first outer profile 82 along the cutting segment 70 of the first body portion 38, and a second outer profile 86 along the guiding segment 74 of the first body portion 38 that is different than the first outer profile 82. The first outer profile 82 is configured to cut into bone so as to form the hole 12, and the second outer profile 86 is configured to primarily act as a guide for the drill bit 10 as the hole 12 is being formed and/or is configured to reduce thermal damage.

As shown in FIG. 2D, the first outer profile 82 has a first leading edge 90, a first trailing edge 94, and a first bearing surface 98 between the first leading edge 90 and the first trailing edge 94. The first leading edge 90 is configured to cut into bone and merges with the first bearing surface 98 such that the first leading edge 90 and the first bearing surface 98 are spaced from the central axis C by a first leading edge length $L_{L1}$ and a first bearing length $L_{B1}$ respectively. The first leading edge length $L_{L1}$ and the first bearing length $L_{B1}$ can be substantially equal to each other so as to define the first radius $R_1$ that is substantially equal to the hole radius R of the hole 12 to be formed. That is, the first bearing surface 98 extends directly from the first leading edge 90 so as to define a curve having a radius that is substantially equal to the radius of the hole to be formed by the drill bit 10. Therefore, as the first leading edge 90 cuts into the bone, the first bearing surface 98 can move along the wall of the hole 12 that is being formed.

As shown in FIG. 2D, the first outer profile 82 further includes a first trailing surface 102 that connects the first trailing edge 94 to the first bearing surface 98. As shown, the first trailing edge 94 is spaced from the central axis C by a first trailing edge length $L_{T1}$ that is less than the first leading edge length $L_{L1}$ (i.e. the first radius $R_1$), such that the first trailing surface 102 is angled radially inward with respect to a tangent of the first bearing surface 98 by an angle $Ø_1$. In the illustrated embodiment, the first trailing surface 102 is angled radially inward with respect to a tangent of the first bearing surface 98 by about 20°. It should be appreciated, however, that the first trailing surface 102 can be angled radially inward with respect to a tangent of the first bearing surface 98 by any angle $Ø_1$ as desired. The trailing surface 102 can be substantially straight as illustrated or the trailing surface 102 can be curved as desired. Because the first trailing edge 94 is spaced radially inward with respect to the first leading edge 90 and because the first trailing surface 102 is angled radially inward, at least a portion of the first outer profile 82 is spaced apart from the wall of the hole 12 as the hole 12 is being formed by the surgical drill bit 10.

Now in reference to FIG. 2E, the second outer profile 86 has a second leading edge 120, a second trailing edge 124, and a second bearing surface 128 between the second leading edge 120 and the second trailing edge 124. The second leading edge 120 is configured to be spaced away from the wall of the hole 12 that is being formed by the drill bit 10. Therefore, the second leading edge 120 can be spaced away from the central axis C by a second leading edge length $L_{L2}$ that is less than the first leading edge length $L_{L1}$ For example, the second leading edge length $L_{L2}$ can be substantially equal to the first trailing edge length $L_{T1}$ as illustrated. It should be appreciated, however, that the second leading edge 120 can be spaced from the central axis by any length $L_{L2}$ as desired so long as a major portion, such as the entire guiding segment 74 has a second leading edge 120 that is spaced radially inward relative to the first leading edge 90. Moreover, it should be appreciated that the second leading edge length $L_{L2}$ can vary along the length of the guiding segment 74 so long as at least a major portion, such as the entire guiding segment 74 has a second leading edge 120 that is spaced radially inward relative to the first leading edge 90.

The second bearing surface 128 like the first bearing surface 98 is spaced from the central axis C by a second bearing length $L_{B2}$ that can be substantially equal to the first bearing length $L_{B1}$ so as to also define the first radius $R_1$ that is substantially equal to the hole radius R of the hole 12 to be formed. That is, the second bearing surface 128 extends about the central axis C so as to define a curve having a radius that is substantially equal to the radius of the hole to be formed by the drill bit 10. Therefore, as the drill bit 10 advances further into the bone, the second leading edge 120 can avoid cutting into the wall of the hole that is being formed and the second bearing surface 128 can move along the wall to thereby act as a guide surface for the drill bit 10. It should be appreciated, that in some embodiments, the second bearing length $L_{B2}$ varies along the length of the guiding segment 74 such that portions of the second bearing surface 128 are configured to move along the wall to thereby act as a guide surface while other portions of the second bearing surface 128 are spaced radially inward relative to the wall and provide substantially no contact with the wall.

The second bearing length $L_{B2}$ also defines the outer radius $R_{2A}$ of the guiding segment 74. Therefore, in embodiments where the outer radius $R_{2A}$ is less than the outer radius $R_{2B}$ of the cutting segment 70 the second bearing length $L_{B2}$ can be less than the first bearing length $L_{B1}$. Therefore, as the drill bit 10 advances further into the bone, the second leading edge 120 can avoid cutting into the wall of the hole that is being formed and the second bearing surface 128 can also be spaced from the wall so as to help reduce thermal damage. It should be appreciated, however, that as the drill bit 10 advances into the bone, the second bearing surface 128 may come into contact with the wall of the hole.

As shown in FIG. 2E, the second outer profile 86 further includes a leading surface 132 that connects the second leading edge 120 to the second bearing surface 128. The leading surface 132 and the second bearing surface 128 intersect at a junction 133. As shown, the leading surface 132 is angled radially inward with respect to a tangent of the second bearing surface 128 taken at the junction 133. The leading surface 132 can be angled by an angle $\varnothing_2$ that can be about 30° as illustrated or any angle as desired. For example, the angle $\varnothing_2$ can be between about 1° and about 60°, or between about 15° and about 45°. The leading surface 132 can be substantially straight as illustrated. It should be appreciated, however, that in some embodiments, the leading surface 132 can be non-linear so as to be curved, ribbed, lobular, etc.

As shown in FIG. 2E, the second outer profile 86 further includes a second trailing surface 142 that connects the second trailing edge 124 to the second bearing surface 128. As shown, the second trailing edge 124 like the first trailing edge 94 is spaced from the central axis C by a second trailing edge length $L_{T2}$ that is less than the first leading edge length $L_{L1}$ (i.e. the first radius $R_1$), such that the second trailing surface 142 is angled radially inward with respect to a tangent of the second bearing surface 128 by an angle $\varnothing_3$. The second trailing surface 142 can be substantially straight as illustrated or the second trailing surface 142 can be curved as desired. Because both the second leading edge 120 and the second trailing edge 124 are spaced radially inward with respect to the first leading edge 90 and because the leading surface 132 and the second trailing surface 142 are angled radially inward at least a majority of the second outer profile 86 is spaced apart from the wall of the hole 12 as the hole 12 is being formed. It should be appreciated that the second trailing edge length $L_{T2}$ can be substantially equal to the first trailing edge length $L_{T1}$ as illustrated, or the first and second trailing edge lengths $L_{T1}$ and $L_{T2}$ can be different as desired or even vary along the lengths of the cutting segment and guiding segment, as desired. Moreover, it should be appreciated that the angle $\varnothing_3$ can be substantially equal to the angle $\varnothing_1$ as illustrated, or the angles $\varnothing_1$ and $\varnothing_3$ can be different as desired.

As shown in FIGS. 2D and 2E, body portion 38 further defines cutout portions 180 between each helical flute 78 that are shaped to move bone chips away from the drill bit tip. The cutout portions 180 can be concave and generally circular in cross-section so as to define a cutout portion radius $R_C$ with respect to the outer radius $R_1$. The cutout portion radius $R_C$ can vary depending on the size of the drill bit and/or the number of flutes. Each cutout portion 180 defines a surface 184 that extends from the leading edge of one flute 78 to the trailing edge of an adjacent flute 78. At the cutting segment 70, each surface 184 merges with a respective first bearing surface 98 at the first leading edge 90 so as to define a first vertex 186 at the first leading edge 90 and also merges with a respective first trailing surface 102 at the first trailing edge 94 so as to define a second vertex 190. Additionally, at the guiding segment 74, each surface 184 merges with a respective leading surface 132 at the second leading edge 120 so as to define a third vertex 192 at the second leading edge 120 and also merges with a respective second trailing surface 142 at the second trailing edge 124 so as to define a fourth vertex 194 at the second trailing edge 124. It should be appreciated, however, that the cutout portions 180 can have any configuration as desired. For example, the cutout portions can be non-circular in cross-section so as to define multiple radii, can be lobular, or can be parabolic, as desired.

With continued reference to both FIGS. 2D and 2E, the first outer profile 82 defines a first outer profile circumferential length $L_{P1}$ and the second outer profile 86 defines a second outer profile circumferential length $L_{P2}$ that is substantially equal to the first outer profile circumferential length $L_{P1}$. For example, the lengths $L_{P1}$ and $L_{P2}$ can be between about 0.25 mm and 0.75 mm. It should be appreciated, however, that the first outer profile 82 and the second outer profile 86 can have any lengths $L_{P1}$ and $L_{P2}$ as desired. Moreover, it should be appreciated, that in some embodiments the lengths $L_{P1}$ and $L_{P2}$ can very along the lengths of the cutting segment and the guiding segment, and therefore, in some embodiments, the lengths $L_{P1}$ and $L_{P2}$ can be different from each other.

As shown in FIGS. 2D and 2E, the first bearing surface 98 can define a first bearing circumferential length $L_{BC1}$ and the second bearing surface 128 can define a second bearing circumferential length $L_{BC2}$ that is substantially less than the first bearing circumferential length $L_{L1}$. For example, the second bearing circumferential length $L_{BC2}$ can be between about 0.10 mm and about 0.20 mm, and the first bearing circumferential length $L_{BC1}$ can be between about 0.20 mm and about 0.30 mm. In the illustrated embodiment, the second bearing circumferential length $L_{BC2}$ is about 0.15 mm, and the first bearing circumferential length $L_{BC1}$ is about 0.25 mm. Therefore, the second bearing circumferential length $L_{BC2}$ can be less than 75% of the first bearing circumferential length $L_{BC1}$, and preferably is less than 60% of the first bearing circumferential length $L_{BC1}$. It should be appreciated, however, that the first and second bearing surfaces 98 and 128 can have any circumferential lengths as desired. Moreover, it should be appreciated that the first and second bearing circumferential lengths $L_{BC1}$ and $L_{BC2}$ can vary along the lengths of the cutting segment 70 and the guiding segment 74.

In operation, the drill bit 10 can be positioned such that the cutting tip 80 is pressed against a target hole location of the bone. When the drill is turned on, the cutting tip 80 and the cutting segment 70 will axially cut into the bone to thereby form the hole 12. As the drill bit 10 is further advanced into the bone, the guiding segment 74 will guide the drill bit 10 within the hole without substantially cutting into the wall of the hole 12. For example, the drill bit 10 may maintain a diameter of the hole to within 10% of a desired diameter when the drill bit is operated at 90,000 rpm. Moreover, because of the reduced second bearing surface 128, less heat may be created by the drill bit thereby reducing the risk of thermal damage. The drill bit 10 can be provided in a kit having a plurality of the drill bits 10, each having a different outer radius $R_1$ so that a variety of sized holes 12 can be made. The drill bit 10 can also be provided in a kit having a load carrier, at least one bone screw and/or a drill that is configured to rotate the drill bit 10.

The drill bit 10 can be manufactured as a single monolith unit. For example, first a drill bit having identical flutes winding around a center axis can be manufactured using conventional methods of manufacture. The cutting segment 70 can then be masked and the guiding segment 74 can then be altered for example by breaking the leading edge of the flutes along the guiding segment 74 so as to create the second leading edge 120 and the leading surface 132. The leading edges of the flutes 78 along the guiding segment 74 can be broken using any method desired. For example, the leading edges 120 can be bead blasted, chamfered, cut, chiseled, beveled, or chemically etched. It should be appreciated, however, that the surgical drill bit 10 can be manufactured using any method as desired.

Figure 3A:
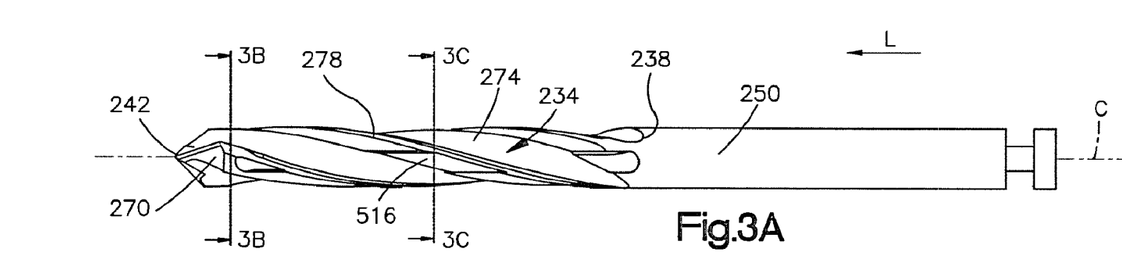
FIG. 3A is a side perspective view of a surgical drill bit constructed in accordance with another embodiment, the surgical drill bit having a guiding segment that has bearing surfaces that are spaced from a center axis of the surgical drill bit by a length that varies along the guiding segment.
Figure 3B:
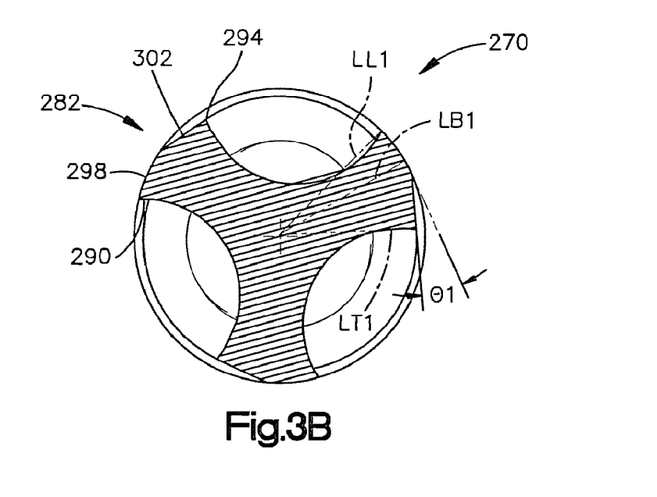
FIG. 3B is a cross-sectional view of the surgical drill bit shown in FIG. 3A through the line 3B-3B and showing an outer profile of the flutes along the cutting segment of the body portion.
Figure 3C:
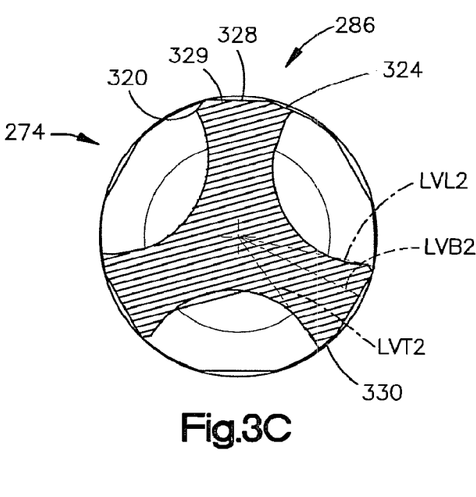
FIG. 3C is a cross-sectional view of the surgical drill bit shown in FIG. 3A through the line 3C-3C and showing an outer profile of the flutes along the guiding segment of the body portion.

In accordance with another embodiment, and in reference to FIGS. 3A-3C, a surgical drill bit 210 can include a guiding segment that is configured to further reduce the amount of the guiding segment that is in contact with the hole wall while still maintaining a portion of the guiding segment in contact with the hole wall. Moreover, the surgical drill bit 210 can be configured to reduce any friction that may be caused by debris from the cut bone as the debris is riding up the helical flutes and out of the hole. The drill bit 210 is similar to the drill bit 10 and includes like structure unless otherwise described.

As shown in FIG. 3A, the drill bit 210 includes a body 234 that is elongate along the longitudinal direction L. The body 234 includes a first cylindrical body portion 238 that is elongate along the longitudinal direction L and defines a distal end 242, and a proximal end 246 spaced from the distal end 242 along the longitudinal direction L. The body 34 further includes a second body portion 250 that extends from the proximal end 246 of the first body portion 238. The first body portion 238 and the second body portion 250 further define a central axis C that extends along the longitudinal direction L. The first body portion 238 and the second body portion 250 can be integrally formed as a monolithic unit.

As shown in FIG. 3A, the first body portion 238 is separated along the longitudinal direction L into a distal cutting segment 270, and a guiding segment 274 that is proximal to the cutting segment 270. The first body portion 238 can include at least one, such as three helical flutes 278 that wind about the central axis C from the distal end 242 to the proximal end 246 of the first body portion 238. As shown, the distal end 242 of the first body portion 238 defines a cutting tip 280 of the first body portion 238. While the first body portion 238 is illustrated as including three helical flutes 278 it should be appreciated that the first body portion 238 can include any number of flutes 278 as desired. For example, the first body portion 238 can include two or four helical flutes 278.

Now in reference to FIGS. 3A-3C, each helical flute 278 defines a first outer profile 282 along the cutting segment 270 of the first body portion 238, and a second outer profile 286 along the guiding segment 274 of the first body portion 238. The first outer profile 282 is configured to cut into bone so as to form the hole 12, and the second outer profile 286 is configured to primarily act as a guide for the drill bit 210 as the hole 12 is being formed. The distance by which the flutes 278 are spaced from the central axis C varies along the guiding segment 274 so as to further reduce heat buildup at high speeds.

As shown in FIG. 3B the first outer profile 282 has a first leading edge 290, a first trailing edge 294, and a first bearing surface 298 between the first leading edge 290 and the first trailing edge 294. The first leading edge 290 is configured to cut into bone and merges with the first bearing surface 298 such that both the first leading edge 290 and the first bearing surface 298 are spaced from the central axis C by a first leading edge length $L_{L1}$ and a first bearing length $L_{B1}$, respectively that are substantially identical so as to define the first radius $R_1$ that is substantially equal to the hole radius R of the hole 12 to be formed.

As shown in FIG. 3B, like the first outer profile 82 the first outer profile 282 further includes a first trailing surface 302 that connects the first trailing edge 294 to the first bearing surface 298. As shown, the first trailing edge 294 is spaced from the central axis C by a first trailing edge length $L_{T1}$ that is less than the first length $L_{L1}$ (i.e. the first radius $R_1$), such that the first trailing surface 302 is angled radially inward with respect to a tangent of the first bearing surface by an angle $\emptyset_1$. In the illustrated embodiment, the first trailing surface 302 is angled radially inward with respect to a tangent of the first bearing surface 98 by about 20°. The trailing surface 302 can be substantially straight as illustrated or the trailing surface 302 can be curved as desired. Because the first trailing edge 294 is spaced radially inward with respect to the first leading edge 290 and because the first trailing surface 302 is angled radially inward, at least a portion of the first outer profile 282 is spaced apart from the wall of the hole 12 as the hole 12 is being formed by the surgical drill bit 210.

As shown in FIG. 3C, the second outer profile 286 has a second leading edge 320, a second trailing edge 324, and a second bearing surface 328 between the second leading edge 320 and the second trailing edge 324. The second leading edge 320 is configured to be spaced away from the wall of the hole 12 that is being formed by the drill bit 210. Therefore, the second leading edge 320 can be spaced away from the central axis C by a second leading edge length $L_{VL2}$ that is less than the first leading edge length $L_{L1}$. The second leading edge length $L_{VL2}$ can vary along the guiding segment 274. That is, the second leading edge length $L_{VL2}$ varies such that portions of the second leading edge 320 are closer to the hole wall than other portions of the second leading edge 320 along the guiding segment 274. It should be appreciated, that while in the illustrated embodiment the second leading edge length $L_{VL2}$ is always less than the first leading edge length $L_{L1}$, in some embodiments a portion of the second leading edge 320 can have a second leading edge length $L_{VL2}$ that is substantially equal to the first leading edge length $L_{L1}$.

The second bearing surface 328 is spaced from the central axis C by a second bearing length $L_{VB2}$. The second bearing length $L_{VB2}$ can vary along the guiding segment 274 such that portions 329 of the second bearing surface 328 along the helical path will be spaced radially inward with respect to the first bearing surface 298 by a length that is less than the first bearing length $L_{VB1}$, and portions 330 of the second bearing surface 328 along the helical path will be spaced from the central axis such that the second bearing length $L_{VB2}$ is substantially equal to the first bearing length $L_{B1}$. Therefore at any given cross section of the guiding segment 274, the second bearing length $L_{VB2}$ of at least one of the three helical flutes 278 can be different than the second bearing length $L_{VB2}$ of at least one of the other three helical flutes 278 along the guiding segment 274.

The portions of the helical flutes 278 that have the second bearing surfaces 328 that are spaced from the central axis C by a second bearing length $L_{VB2}$ that is equal to the first bearing length $L_{B1}$ define the first radius $R_1$ that is substantially equal to the hole radius R of the hole 12 to be formed. That is, these portions of the helical flutes 278 can include a second bearing surface 328 that extends about the central axis C so as to define a curve having a radius that is substantially equal to the radius of the hole to be formed by the drill bit 210. Therefore, as the surgical drill bit 210 advances further into the bone, the second leading edge 320 can avoid cutting into the wall of the hole that is being formed and portions of the second bearing surface 328 can move along the wall to thereby act as a guide surface for the surgical drill bit 210.

The portions of the helical flutes 278 that have second bearing surfaces 328 that are spaced from the central axis C by a second bearing length $L_{VB2}$ that is less than the first bearing length $L_{B1}$ are configured to be spaced from the wall of the hole 12 being formed. These portions of the helical flutes can include a second bearing surface 328 that is curved so as to define a radius, or substantially straight, as illustrated. Because these portions of the second bearing surface 328 are spaced from the wall of the hole 12 friction caused by debris from cut bone as the surgical drill bit forms the hole 12 and rides up the helical flutes 278 will be reduced. That is, the amount of debris that gets wedged between the surgical drill bit 210 and the hole wall will be reduced due to the gap between the second bearing surface 328 and the hole wall.

As shown in FIG. 3C, at least portions of the second trailing edge 324 and the second bearing surface 328 merge so as to define a substantially planar surface that is spaced from the wall of the hole to be formed. It should be appreciated, however, that the second outer profile 286 can further include a second trailing surface that connects the second trailing edge 324 to the second bearing surface 328. For example, the second trailing edge 324 can be spaced from the central axis C by a second trailing edge length $L_{VT2}$ that is less than the first leading edge length $L_{L1}$ (i.e. the first radius $R_1$), such that the second trailing surface is angled radially inward with respect to a tangent of the first bearing surface by an angle $\emptyset_1$. As with the second leading edge length $L_{VL2}$ and the second bearing length $L_{VB2}$, the second trailing edge length $L_{VT2}$ can vary along the guiding segment 274.

Figure 4A:
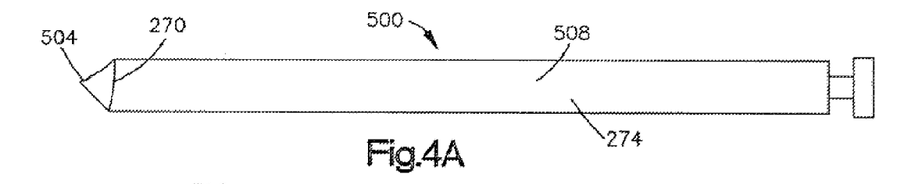
FIG. 4A is a side perspective of a turned blank prior to flutes being cut in the turned blank.
Figure 4B:
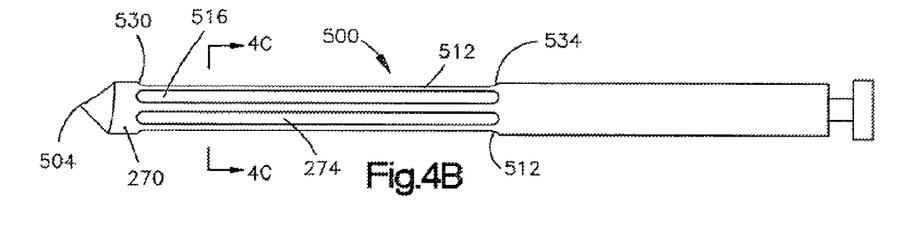
FIG. 4B is a side perspective view of the turned blank shown in FIG. 4A prior to the flutes being cut in the turned blank but after a guiding segment portion of the turned blank has been reduced to define a hexagon in cross-section.
Figure 4C:
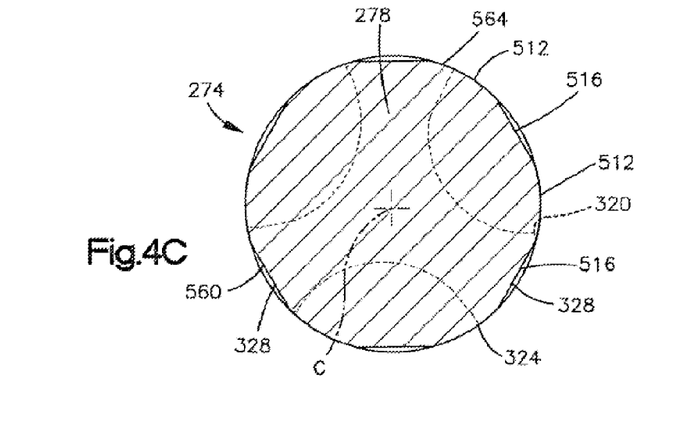
FIG. 4C is a cross-sectional view of the blank shown in FIG. 4B through the line 4C-4C and showing flutes to be formed in phantom lines.

Now in reference to FIGS. 4A-4C, the surgical drill bit 210 can be manufactured by first turning a blank, such as blank 500 shown in FIG. 4A. As shown, the blank 500 includes a tip 504 and a cylindrical body 508 that is elongate along the longitudinal direction L. The cylindrical body 508 includes the cutting segment 270 and the guiding segment 274.

As shown in FIGS. 4B and 4C, the guiding segment 274 of the cylindrical body 508 can be further turned or otherwise reformed to define a noncircular cross-section prior to the flutes 278 being formed. For example, as shown, the cylindrical body 508 can be reformed so as to define a substantially hexagonal cross-section such that about six outer surfaces 512 define an outer radius of the cylindrical body 508, and about six substantially flat surfaces 516 that connect adjacent outer surfaces 512 together. As shown, the flat surfaces 516 are recessed radially inward with respect to the outer radius of the cylindrical body 508. It should be appreciated, however, that the cylindrical body 508 can be reformed so as to define other noncircular cross-sections. For example, the cylindrical body 508 can be reformed to define a substantially square, triangular, ovular, or lobular shaped cross-section. It should also be appreciated that the body 508 can be turned or otherwise reformed to define the non-circular cross-section after the flutes 278 have been formed. Therefore, the steps of making the drill bit 210 can be performed in any particular order.

As shown in FIG. 4B, at least a portion, such as the entire length of the guiding segment 274 can be reformed to define the non-circular cross-section. For example, the guiding segment 274 can be reformed from a distal end 530 of the guiding segment 274 up to a position that is distal to a proximal end 534 of the guiding segment 274, from a position that is proximal to the distal end 530 to the proximal end 534, or from a position that is proximal to the distal end 530 to a position that is distal to the proximal end 534.

As shown in FIG. 4C, the flutes 278 can be cut into the body 508 such that the flutes 278 wind about the central axis of the body 508 so as to form the surgical drill bit 210. As shown, an outer radius of the flutes 278 along the guiding segment 274 with respect to the central axis C will vary as the flutes wind about the central axis C. Therefore, the second bearing surface 328 of the flutes 278 will be spaced from the central axis C by a varying length such that portions 560 of the second bearing surface 328 will be spaced radially inward with respect to the first bearing surface 298, and portions 564 of the second bearing surface 328 will be spaced from the central axis C the same distance as the first bearing surface 298. Because of the hexagonal cross-section, the second outer profile 286 of each flute 278 will be substantially sinusoidal with each flute 278 being out of phase with the other flutes 278. It should be appreciated, however, that the portions of the second outer profile 286 that are formed along the angled surfaces can be substantially flat.

Because of the varying spacing of the second outer profile 286 and in particular the second bearing surface 328 at any given cross section of the guiding segment 274, at least the second bearing length $L_{B2}$ of at least one of the three helical flutes 278 is different than the second bearing length $L_{B2}$ of at least one of the other three helical flutes 278. For example, at the cross-section shown in FIG. 4C, the entire second profile 286 of two of the helical flutes 278 is spaced radially inward from the outer radius of the surgical drill bit 210, while the second outer profile 286 of one of the helical flutes 278 includes a portion of the second bearing surface 328 that is substantially equal to the outer radius of the surgical drill bit 210.

In operation, the surgical drill bit 210 can be positioned such that the cutting tip 280 is pressed against a target hole location of the bone. When the drill is turned on, the cutting tip 280 and the cutting segment 270 will axially cut into the bone to thereby form the hole 12. As the surgical drill bit 210 is further advanced into the bone, the guiding segment 274 will guide the drill bit 210 within the hole without substantially cutting into the wall of the hole 12. Moreover, because of the reduced second bearing surface 328 and because portions of the second bearing surface 328 are spaced from the wall of the hole 12, less heat may be created by the drill bit 210 thereby reducing the risk of thermal damage. The surgical drill bit 210 can be provided in a kit having a plurality of the drill bits 210, each having a different outer radius $R_1$ so that a variety of sized holes 12 can be made. The drill bit 210 can also be provided in a kit having a load carrier, at least one bone screw and/or a drill that is configured to rotate the drill bit 210. Moreover over the surgical drill bit 10 and the surgical drill bit 210 can provided as a kit alone or with any of a load carrier, a bone screw, and a drill.

While the foregoing description and drawings represent the preferred embodiments of the present invention, it will be understood that various additions, modifications, combinations and/or substitutions may be made therein without departing from the spirit and scope of the invention as defined in the accompanying claims. In particular, it will be clear to those skilled in the art that the invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components, which are particularly adapted to specific environments and operative requirements without departing from the principles of the invention. In addition, features described herein may be used singularly or in combination with other features. For example, features described in connection with one embodiment may be used and/or interchanged with features described in another embodiment. The presently disclosed embodiments are therefore to be considered in all respects as illustrative and not restrictive, the scope of the invention being indicated by the appended claims, and not limited to the foregoing description.

It will be appreciated by those skilled in the art that various modifications and alterations of the invention can be made without departing from the broad scope of the appended claims. Some of these have been discussed above and others will be apparent to those skilled in the art. For example, the features of the drill bit can also be incorporated into a screw, a reamer, or even a K-wire.

What is claimed:

1. A surgical drill bit configured to form a hole in an anatomical structure, the surgical drill bit comprising:
an elongate cylindrical body portion that defines a proximal end, a distal end spaced from the proximal end along a central axis, and at least one flute that extends helically about the central axis from the distal end to the proximal end, the body portion further defining a cutting segment and a guiding segment that is proximal to the cutting segment, wherein the at least one flute defines:
a first outer profile at the cutting segment, the first outer profile defining a first leading edge that is configured to cut into bone, and a first bearing surface that extends from the first leading edge such that both the first leading edge and the first bearing surface are spaced from the central axis by a first length that substantially defines a radius of the hole, and
a second outer profile at the guiding segment, the second outer profile defining:
i) a second leading edge that is spaced from the central axis by a second leading edge length that is less than the first length,
ii) a second bearing surface that is spaced from the central axis by a second bearing length that is greater than the second leading edge length, and
iii) a substantially straight leading surface that is connected between the second leading edge and the second bearing surface.

2. The surgical drill bit of claim 1, wherein the first outer profile further defines a first trailing edge and the second outer profile further defines a second trailing edge.

3. The surgical drill bit of claim 2, wherein the first trailing edge and the second trailing edge are each spaced from the central axis by a trailing edge length that is substantially equal to the second leading edge length.

4. The surgical drill bit of claim 1, wherein the leading surface defines a first angle with respect to a tangent of the second bearing surface, and the first angle is between about 1° and about 60°.

5. The surgical drill bit of claim 4, wherein the first angle is between about 15° and 45°.

6. The surgical drill bit of claim 4, wherein the leading surface and the second bearing surface intersect at a junction, and the tangent is taken at the junction.

7. The surgical drill bit of claim 1, wherein the first bearing surface has a first circumferential length, and the second bearing surface has a second circumferential length that is less than the first circumferential length.

8. The surgical drill bit of claim 7, wherein the second circumferential length is less than 75% of the first circumferential length.

9. The surgical drill bit of claim 8, wherein the second circumferential length is less than 60% of the first circumferential length.

10. The surgical drill bit of claim 7, wherein the second circumferential length is between 0.10 mm and about 0.20 mm.

11. The surgical drill bit of claim 1, wherein the cutting segment defines a cutting segment length along the central axis, and the guiding segment defines a guiding segment length along the central axis, and wherein the cutting segment length is less than 35% of the guiding segment length.

12. The surgical drill bit of claim 1, wherein the body portion includes three substantially identical helical flutes.

13. The surgical drill bit of claim 12, wherein the body portion further includes a respective cutout portion between adjacent helical flutes, each cutout portion having a surface that (i) at the cutting segment extends from the first leading edge of one of the three helical flutes to the first trailing edge of an adjacent one of the three helical flutes, and (ii) at the guiding segment extends from the second leading edge of the one of the three helical flutes to the trailing edge of the adjacent one of the three helical flutes.

14. The surgical drill bit of claim 13, wherein the leading surface merges with the surface at the second leading edge such that the second leading edge defines a vertex.

15. The surgical drill bit of claim 1, wherein the second bearing length is substantially equal to the first length.

16. The surgical drill bit of claim 1, wherein the cutting segment defines a first outer radius and the guiding segment defines a second outer radius that is less than the first outer radius.

17. The surgical drill bit of claim 16, wherein the second outer radius is about 0.1 mm less than the first outer radius.

18. A surgical drill bit configured to form a hole in an anatomical structure, the surgical drill bit comprising:
an elongate cylindrical body portion defining a proximal end, a distal end spaced from the proximal end along a central axis, the body portion further defining a cutting segment and a guiding segment that is proximal to the cutting segment, the body portion including at least one flute that extends helically about the central axis from the distal end to the proximal end, the at least one flute defining:
(i) a first outer profile at the cutting segment, the first outer profile having a first leading edge that is configured to cut into bone, and a first bearing surface that extends circumferentially from the leading edge along a first circumferential length, wherein the first bearing surface is spaced from the central axis by a first length that is substantially equal to a radius of the hole to be formed, and
(ii) a second outer profile at the guiding segment, the second outer profile having a second leading edge that is spaced closer to the central axis than the first leading edge, and a second bearing surface that extends circumferentially with respect to the second leading edge along a second circumferential length that is less than 75% of the first circumferential length, wherein the second bearing surface is spaced from the central axis by a second bearing length that is less than or equal to the first bearing length.

19. The drill bit of claim 18, wherein (i) the first leading edge merges with the first bearing surface such that both the first leading edge and the first bearing surface are spaced from the central axis by the first length, (ii) the second leading edge is spaced from the central axis by a second leading edge length that is less than the first length, and (iii) the second outer profile further includes a substantially straight leading surface that connects the second leading edge to the second bearing surface.

20. The surgical drill bit of claim 19, wherein the first outer profile further includes a first trailing edge and the second outer profile further includes a second trailing edge, the first trailing edge and the second trailing edge are each spaced from the central axis by a trailing edge length that is substantially equal to the second leading edge length.

21. The surgical drill bit of claim 19, wherein the leading surface and the second bearing surface intersect at a junction, and the leading surface defines an angle with respect to a tangent of the second bearing surface taken at the junction that is between about 15° and about 45°.

22. The surgical drill bit of claim 18, wherein the second circumferential length is less than 60% of the first circumferential length.

23. The surgical drill bit of claim 18, wherein the second circumferential length is between 0.10 mm and about 0.20 mm.

24. The surgical drill bit of claim 18, wherein the cutting segment defines a cutting segment length along the central axis, and the guiding segment defines a guiding segment length along the central axis, and wherein the cutting segment length is less than 35% of the guiding segment length.

25. The surgical drill bit of claim 18, wherein the body portion includes three substantially identical helical flutes.

26. The surgical drill bit of claim 18, wherein the first bearing length defines an outer radius of the cutting segment and the second bearing length defines an outer radius of the guiding segment, and the outer radius of the guiding segment is less than the outer radius of the cutting segment.

27. The surgical drill bit of claim 26, wherein the outer radius of the guiding segment is about 0.1 mm less than the outer radius of the cutting segment.

28. A surgical drill bit configured to form a hole in an anatomical structure, the surgical drill bit comprising:
   an elongate cylindrical body portion defining a proximal end, a distal end spaced from the proximal end along a central axis, the body portion further defining a cutting segment and a guiding segment that is proximal to the cutting segment, the body portion including at least one flute that extends along a helical path about the central axis from the distal end to the proximal end, the at least one flute defining:
   (i) a first outer profile at the cutting segment, the first outer profile having a first leading edge that is configured to cut into bone, and a first bearing surface that extends from the first leading edge and is spaced from the central axis by a first length that is substantially equal to a radius of the hole, and
   (ii) a second outer profile at the guiding segment, the second outer profile having a second leading edge that is spaced closer to the central axis than the first leading edge, and a second bearing surface that is spaced from the central axis by a length that varies along the helical path at the guiding segment, such that at least one portion of the second bearing surface along the helical path is spaced from the central axis a second length that is less than the first length, and at least one other portion of the second bearing surface along the helical path is spaced from the central axis a third length that is equal to the first length.

29. The surgical drill bit of claim 28, wherein the first bearing surface defines a first circumferential length and the second bearing surface defines a second circumferential length that is less than 75% of the first circumferential length.

30. The surgical drill bit of claim 28, wherein the second circumferential length is less than 60% of the first circumferential length.

31. The surgical drill bit of claim 28, wherein the second circumferential length is between 0.10 mm and about 0.20 mm.

32. The surgical drill bit of claim 28, wherein (i) the first leading edge merges with the first bearing surface such that both the first leading edge and the first bearing surface are spaced from the central axis by the first length, (ii) the second leading edge is spaced from the central axis by a leading edge length that is less than the first length, and (iii) the second outer profile further includes a substantially straight leading surface that connects the second leading edge to the second bearing surface.

33. The surgical drill bit of claim 28, wherein the body portion includes three helical flutes.

34. The surgical drill bit of claim 33, wherein at a cross section of the guiding segment, the second length of at least one of the three helical flutes is different than the second length of at least one of the other three helical flutes.

* * * * *